United States Patent [19]
Chen et al.

[11] Patent Number: 5,874,577
[45] Date of Patent: Feb. 23, 1999

[54] METHOD FOR THE PREPARING [9-12-(DIETHOXYPHOSPHONOMETHOXY) ETHYL]ADENINE AND ANALOGUES THEREOF

[75] Inventors: Wei Chen, Naperville; Michael T. Flavin, Darien; Ze-Qi Xu, Naperville, all of Ill.

[73] Assignee: MediChem Research, Inc., Lemont, Ill.

[21] Appl. No.: 831,922

[22] Filed: Apr. 2, 1997

Related U.S. Application Data

[60] Provisional application No. 60/014,765 Apr. 3, 1996.
[51] Int. Cl.$^6$ ............................. C07F 9/08; C07D 473/34
[52] U.S. Cl. ......................... 544/232; 544/244; 544/277
[58] Field of Search ................................. 544/244, 277, 544/232

[56] References Cited

PUBLICATIONS

Jenny, T. F.; Previsani, N.; Benner, S.A. *Tetrahedron Lett.* 1991, 32, 7029–7032.
Bonnal, C.; Chavis, C.; Lucas, M. *J. Chem. Soc. Perkin Trans.* 1 1994, 1401–1410.
Overberger, C. G.; Chang, J. Y. *Tetrahedron Lett.* 1989, 30, 51–54.
De Clercq, E.; Holy, A.; Rosenberg, I.; Sakuma, T.; Balzarini, J.; Maudgal, P. C.
De Clercq, E.; Sakuma, T.; Baba, M.; Pauwels, R.; Balzarini, J.; Rosenberg, I.; Holy, A. *Antiviral Res.* 1987, 8, 261–272.
Heijtink, R. A.; Kruining, J.; De Wilde, G. A.; Balzarini, J.; De Clercq, E.; Schalm. S. W. *Antimicrob. Agents Chemother.* 1994, 38, 2180–2182.
Pauwels, R.; Balzarini, J.; Schols, D.; Baba, M.; Desmyter, J.; Rosenberg, I.; Holy, A.; De Clercq, E. *Antimicrob. Agents Chemother.* 1988, 32, 1025–1030.
Balzarini, J.; Naesens, L.; Herdewijn, P.; Rosenbeg, I.; Holy, A.; Pauwels, R.; Baba, M.; Jones, D. G.; De Clercq, E. *Proc. Natl. Acad. Sci. USA* 1989, 86, 332–336.
Gong, Y.-F.; Marshall, D. R.; Srinivas, R. V.; Fridland, A. *Antimicrob. Agents Chemother.* 1994, 38, 1683–1687.
Holy, A. Rosenberg, I. *Collect. Czech. Chem. Commun.* 1987, 52, 2801–2809.
Holy, A.; De Clercq, E.; Votruba, I. In *Nucleotide Analogues as Antiviral Agents;* Martin, J. C. Ed.; ACS Washington, D.C., 1989; Chapter 4, pp. 51–71.
Bailey, W. F.; Zarcone, L. M.; Rivera, A. D. *J. Org. Chem.* 1995, 60, 2532–2536.
Arbuzov, B. A.; Ukhvatova, E. N. *Zh. Obshch. Khim.* 1959, 29, 503–507.
Chen, W., et al. (1996), "An Improved Synthesis of 9-[2-(Diethoxyphosphonomethoxy)Ethyl]Adenine and its Analogues with other Pruine Bases Utilizing the Mitsunobu Reaction," *Nucleosides & Nucleotides*, 15(11&12), pp. 1771–1778.
Bailey, W. F., et al. *J. Org. Chem.* 1984, 49, 4958–4964.
Bronson, J. J., et al. *Phosphyonylmethoxyethyl Derivatives of Purine*, 1989, 72–87.
Tsunoda, T., et al. *Tetrahedron Lettes*, 1995, vol. 36, No. 14, 2529–2530.

*Primary Examiner*—Johann Richter
*Assistant Examiner*—Dominic Keating
*Attorney, Agent, or Firm*—McDonnell Boehnen Hulbert & Berghoff

[57] ABSTRACT

Unprotected adenine, 6-chloropurine, 2,6-diaminopurine, and 2-amino-6-chloropurine have been directly coupled with 2-(diethoxyphosphonomethoxy)ethanol under a disclosed method to provide acyclic phosphonate nucleotide analogues which are intermediates for antiviral agents such as 9-[2-(phosphonomethoxy)ethyl]adenine (PMEA) and its analogues having a structure of formula I:

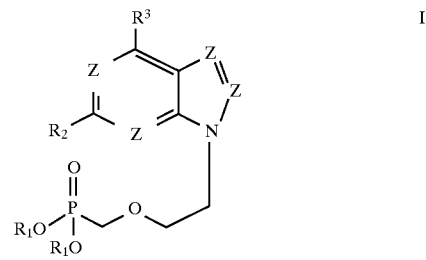

wherein Z represents N or CH; $R_1$ represents hydrogen, alkyl, aryl, or arylalkyl; $R_2$ and $R_3$ are independently selected from H, OH, halo, $NH_2$, $C_6H_5CH_2O$, or $R_4R_5N$ wherein $R_4$ and $R_5$ are independently selected from alkyl, aryl, or arylalkyl.

6 Claims, No Drawings

METHOD FOR THE PREPARING [9-12-(DIETHOXYPHOSPHONOMETHOXY)ETHYL]ADENINE AND ANALOGUES THEREOF

CROSS-REFERENCE

This application is a continuation-in-part of Provisional Application Ser. No. 60/014,765, filed Apr. 3, 1996.

FIELD OF THE INVENTION

The present invention relates to a method for preparing anti-viral agent 9-[2-(phosphonomethoxy)ethyl]adenine (PMEA) and its analogues with other purine bases. The work described in this application was supported, in part, by a Small Business Innovation Research (SBIR) Grant (1 R43 AI 37349) from the National Institutes of Health, Bethesda, Md.

BACKGROUND OF THE INVENTION

PMEA and (S)-9-[3-hydroxy-2-(phosphonomethoxy)propyl]adenine [(S)-HPMPA] have been reported to exhibit potent and selective activity against a broad spectrum of viruses,[5,6] including herpes simplex virus (types 1 and 2), varicella zoster virus, cytomegalovirus, hepatitis B virus,[7] as well as human immunodeficiency virus (HIV).[8-10] These compounds have been prepared by classical coupling of adenine,[11-13] or its precursors such as 6-chloropurine, with an appropriate phosphonate side chain (2) in the presence of a base such as NaH, $K_2CO_3$, or $Cs_2CO_3$ at elevated temperatures, followed by hydrolysis. However, coupling reactions under these basic conditions often yield both $N^7$- and $N^9$-substituted derivatives;[11-13] the adenine salt generated during the reaction course also attacks the phosphonate ethyl ester to form $N^9$-ethyladenine.[13] Accordingly, there is a need for an efficient method for preparing PMEA and analogues thereof with less side product contamination and under mild conditions.

SUMMARY OF THE INVENTION

The present invention relates to an efficient method for the preparation of 9-[2-(diethoxyphosphonomethoxy)ethyl]adenine (PMEA) under Mitsunobu conditions, as well as the application of this method to the synthesis of other purine derivatives. Although the Mitsunobu reaction has been widely used in the synthesis of nucleosides and nucleotides starting with protected purines and pyrimidines,[1-4] none of the disclosed methods disclose or suggest a method for preparing PMEA and related analogues from unprotected adenine and related unprotected purines such as 6-chloropurine, 2,6-diaminopurine, and 2-amino-6-chloropurine under Mitsunobu conditions.

According to the method of the present invention, free adenine and unprotected purine derivatives such as 6-chloropurine, 2,6-diaminopurine, and 2-amino-6-chloropurine were directly coupled for the first time to a variety of free alcohol side chains under Mitsunobu conditions to prepare phosphonate nucleotide analogues which, upon hydrolysis, led to formation of anti-viral agent PMEA and its analogues as shown in Formula I:

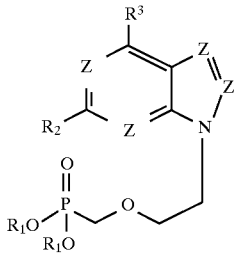

wherein Z represents N or CH; $R_1$ represents hydrogen, alkyl, aryl, or arylalkyl and $R_2$ and $R_3$ are independently selected from H, OH, halo, $NH_2$, $C_6H_5CH_2O$, or $R_4R_5N$ wherein $R_4$ and $R_5$ are independently selected from alkyl, aryl, arylalkyl, or $R_1CO$.

DETAILED DESCRIPTION OF THE INVENTION

All literature, patents and patent applications cited herein are hereby incorporated by reference in their entirety.

The present invention relates to a method for preparing anti-viral agent PMEA and its analogues as shown in Formula I:

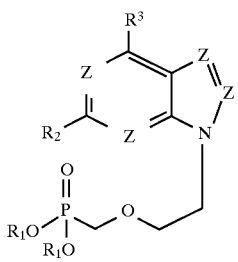

wherein Z represents N or CH; $R_1$ represents hydrogen, alkyl, aryl, or arylalkyl and $R_2$ and $R_3$ are independently selected from H, OH, halo, $NH_2$, $C_6H_5CH_2O$, or $R_4R_5N$ wherein $R_4$ and $R_5$ are independently selected from alkyl, aryl, arylalkyl, or $R_1CO$. As defined herein, alkyl refers to branched or linear $C_{1-6}$; aryl refers to phenyl or substituted phenyls including mono, di, and trisubstituted phenyls such as 4-methoxyphenyl and 4-chlorophenyl; and arylalkyl includes phenylalkyls and substituted phenylalkyls such as benzyl, triphenylmethyl, 4-methoxytriphenylmethyl, and 4,4'-dimethoxytriphenylmethyl.

According to the method of the present invention as illustrated in Scheme 1 below, free adenine and unprotected related purine derivatives such as 6-chloropurine, 2,6-diaminopurine, and 2-amino-6-chloropurine were directly coupled for the first time to a variety of free alcohol side chains under Mitsunobu conditions to prepare phosphonate nucleotide analogues which, upon hydrolysis, led to formation of anti-viral agent PMEA and its analogues.

Thus, the free alcohol side chain 2b, required for the Mitsunobu reaction, was prepared by literature procedures in a 3-step process, starting from 1,3-dioxolane, 3;[11] however, a modified method[14,15] utilizing a catalytic amount of $ZnCl_2$ was found to be more effective for acylative cleavage of 3 to yield chloromethyl ether 4 (Scheme 1).

Thereafter, 2b is coupled with adenine to produce 1a under modified Mitsunobu conditions. In performing this reaction, diethyl azodicarboxylate (DEAD) was added dropwise to a solution containing 1a and triphenylphosphine at a temperature ranging between about −78° C. and about 40° C., preferably about ambient temperature. The amount of DEAD used in the reaction generally ranges between about 1 mole and about 10 moles preferably about 1 mole and about 4 moles, per mole of 1a. The amount of triphenylphosphine used in the reaction generally ranged between about 1 mole and about 10 moles, preferably ranging between about 1 mole and about 4 moles, per mole of 1a.

and/or stained with iodine. Column chromatography was performed using silica gel 60 (70–230 mesh from EM Science). $^1$H and $^{13}$C NMR spectra were recorded on a Varian VX-300 NMR spectrometer or a 300 MHz Varian Gemini 2000 NMR spectrometer. Chemical shifts (δ) are

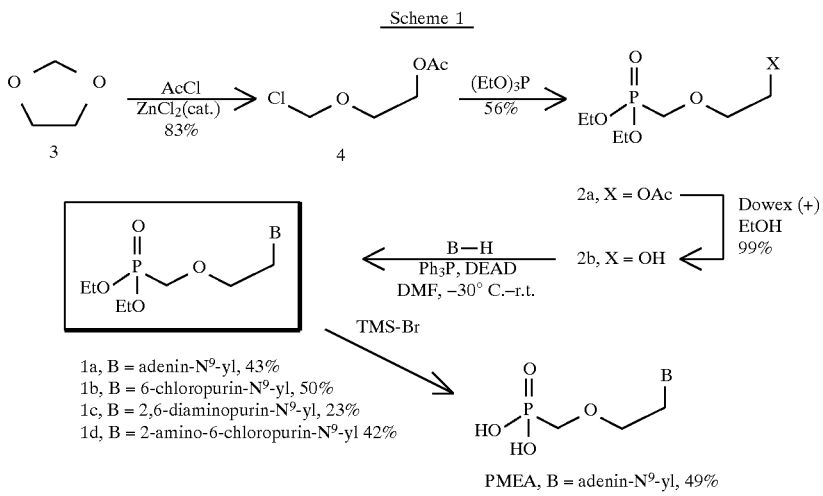

If desired, other suitable azo reagents reported in the literature can be employed in place of DEAD such as diisopropyl azodicarboxylate (DIAD), dibutyl azodicarboxylate (DBAD), dipiperidinoazodicarboxamide,bis($N^4$-methylpiperazin-1-yl)azodicarboxamide, dimorpholinoazodicarboxamide, N,N,N',N'-tetramethylazodicarboxamide (TMAD)[17]. Also, in addition to triphenylphosphine, other phosphine derivatives such as tri-n-butylphosphine,[17] triethylphosphine, trimethylphosphine and tris(dimethylamino)phosphine may be used.

Coupling of 2b with adenine in THF in the presence of Ph$_3$P and DEAD formed the desired $N^9$-substituted derivative 1a in only 5% yield. The low yield may be due to the insolubility of adenine in THF. After replacement of THF with DMF, compound 1a was produced in 43% yield without any detection of the $N^7$- derivative or the $N^9$-ethyladenine.

The same procedure was applied to 6-chloropurine to afford compound 1b in 50% yield. In contrast, when 2,6-diaminopurine was coupled with the side chain 2b under the same conditions, $N^9$-ethyl-2,6-diaminopurine was the major product. It has been found that formation of the desired coupling product 1c depends upon the reaction temperature. Compound 1c became the predominant product, with minimal formation of $N^9$-ethyl-2,6-diaminopurine, when the reaction was carried out at low temperatures, e.g., −20° C. (Scheme 1). The corresponding 2-amino-6-chloropurine derivative 1d was also prepared at −10° C. in 42% yield. The synthesized phosphonate nucleotide analogues (1a–1d) afforded satisfactory analytical and spectroscopic analyses. Hydrolysis of 1a with a trimethylsilyl halide such as TMS-Br led to PMEA.[11-13]

EXAMPLES

The following Examples describe the syntheses of PMEA and intermediates as shown in Scheme 1. Melting points were taken on a Laboratory Devices Mel-Temp apparatus and are corrected. TLC analyses were performed on analytical thin layer plates coated with silica gel 60 F$_{254}$ (Merck) and components were visualized under UV light expressed in ppm from Me$_4$Si as an internal standard and were recorded in CDCl$_3$ solution unless otherwise stated. IR and mass spectra were recorded on a Midac M series FT-IR and a Finnegan MAT 90 mass spectrometer, respectively. UV spectra were measured in MeOH or aqueous solutions on a Hitachi U-2000 UV-VIS spectrophotometer. Elemental analyses were carried out at Midwest Microlab, Indianapolis, Ind. All chemical reagents and anhydrous solvents were purchased from Aldrich Chemical Co.

Example 1

1-Acetoxy-2-chloromethoxyethane (4).[15,16]

In this Example, 1-acetoxy-2-chloromethoxyethane was prepared based on reported procedures.

To a 25 mL three-necked round bottom flask equipped with an addition funnel, a condenser, a thermometer, and a magnetic stirrer were added 1,3-dioxolane (5.0 g, 67.5 mmol) and a few crystals of freshly fused zinc chloride under N$_2$. A solution of acetyl chloride (5.3 g, 67.5 mmol) in anhydrous hexane (5 mL) was added dropwise to the stirred reaction mixture over 30 min. An exothermic reaction occurred immediately and the reaction temperature was maintained below 50° C. by using an ice-water bath. After addition, the reaction mixture was stirred at ambient temperature for 2 h and then concentrated under reduced pressure and the residue was distilled under vacuum to afford 4 (8.6 g, 83% yield), bp. 57°–59° C./0.3 mm Hg (Lit $^{15}$ 70°–72° C./4.5 mm Hg). $^1$H NMR (CDCl$_3$) δ 5.52 (s, 2 H, CH$_2$Cl), 4.27 (m, 2 H, CH$_2$OAc), 3.90 (m, 2 H, CH$_2$O), 2.10 (s, 3 H, CH$_3$); $^{13}$C NMR (CDCl$_3$) δ 170.78 (CO), 82.51 (CH$_2$Cl), 68.00 (CH$_2$OAc), 62.14 (CH$_2$O), 20.79 (CH$_3$); IR (neat, cm$^{-1}$) 1742 (vs, C═O); MS (CI) m/e 123 and 125 (21.4, 6.3, M—CO), 117 (100, M—Cl).

Example 2

Diethyl 2-Acetoxyethoxymethane-phosphonate (2a).[11,16]

1-Acetoxy-2-chloro-methoxyethane, 4, (96.9 g, 0.583 mol) was added under N$_2$ to a 500 mL three-necked round bottom flask equipped with an addition funnel, a thermometer, and a magnetic stirrer. Triethylphosphite (92.5 g, 0.607 mol) was added dropwise to the stirred solution over a 1 h period. The reaction mixture was heated at 110° C. in an oil-bath for 1 h and then gradually cooled to ambient temperature. Vacuum distillation provided 2a (82.1 g, 55.4% yield) as a colorless liquid, bp. 148°–153° C./0.6 mm Hg (Lit.[15] 136°–137.5° C./1.5 mm Hg). $^1$H NMR (CDCl$_3$) δ 4.24 (t, J=4.7 Hz, 2 H, CH$_2$OAc ), 4.17 (q, J=7.6 Hz, 4 H, 2 CH$_2$O), 3.85 (d, J=8.2 Hz, 2 H, CH$_2$P), 3.81 (t, J=4.7 Hz, 2 H, CH$_2$O), 2.08 (s, 3 H, CH$_3$CO), 1.36 (t, J=7.1 Hz, 6 H, 2 CH$_3$); $^{13}$C NMR (CDCl$_3$) δ 170.86 (CO), 70.97 (d, $^{2J}$C,P=10.5 Hz, CH$_2$O), 65.25 (d, $^{2J}$C,P=166.2 Hz, CH$_2$P), 63.20 (CH$_2$OAc), 62.49 (d, $^{3J}$C,P=6.5 Hz, CH$_2$O), 20.85 (CH$_3$CO), 16.44 (d, $^{3J}$C,P=5.7 Hz, CH$_3$); IR (neat, cm$^{-1}$ 1740 (vs, C=O), 1238 (vs, P=O), 1049 and 1033 (vs, P—O—C and C—O—C); MS (CI) m/e 255 (76.9, M+1), 213 (30.3, M—CH$_2$CO+1), 167 (50.4, M—C$_2$H$_5$O—CH$_3$CO+1), 166 (51.4, M—C$_2$H$_5$O—CH$_3$CO), 153 (100, M—C$_2$H$_5$O—CH$_2$CO—CH$_3$+1), 139 (68.7, M—C$_2$H$_5$O—CH$_2$CO—C$_2$H$_5$+1), 125 (96.6, M-2 C$_2$H$_4$—CH$_3$CO$_2$CH$_2$); Anal. calcd. for C$_9$H$_{19}$O$_6$P: C, 42.52; H, 7.53. Found: C, 42.32; H, 7.61.

Example 3

Diethyl 2-Hydroxyethoxymethane-phosphonate (2b).[11]

To a 500 mL single-necked round bottom flask equipped with a condenser were added diethyl 2-acetylethoxymethanephosphonate, 2a, (30 g, 0.12 mol), ethanol (150 mL) and Dowex 50WX8 (H$^+$-form, 15 g) prewashed with ethanol (4×50 mL). The mixture was heated to reflux for 18 h and completion of the reaction was determined by TLC analysis. The mixture was filtered, the resin washed with ethanol (3×30 mL), and the combined filtrates concentrated under reduced pressure. The residue was co-evaporated with anhydrous toluene (2×50 mL) under reduced pressure and dried under vacuum overnight to yield 2b (24.8 g, 99% yield). $^1$H NMR (CDCl$_3$) δ 4.19 (apparent quintet, J=7.3 Hz, 4 H, 2 CH$_2$O), 3.89 (s, 1 H, OH), 3.87 (d, J=8.1 Hz, 2 H, CH$_2$P), 3.70–3.77 (m, 4 H, 2 CH$_2$O), 1.36 (t, J=7.1 Hz, 6 H, 2 CH$_3$); $^{13}$C NMR (CDCl$_3$) δ 75.7 (d, $^{2J}$C,p=10.1 Hz, CH$_2$O), 65.28 (d, $^{1J}$C,p=166.9 Hz, CH$_2$P), 62.59 (d, $^{3J}$C,P=6.6 Hz, CH$_2$O), 61.46 (CH$_2$OH), 16.43 (d, $^{3J}$C,P=5.7 Hz, CH$_3$); IR (neat, cm$^{-1}$) 3408 (vs, broad, OH), 1233 (vs, P=O), 1053 and 1024 (vs, P—O—C and C—O—C); MS (CI) m/e 213 (100, M+1); Anal. calcd. for C$_7$H$_{17}$O$_5$P: C, 39.63; H, 7.86. Found: C, 39.23; H 7.94.

Example 4

9-(2-Diethoxyphosphonomethoxyethyl) adenine (1a)[11]

A mixture of adenine (3.2 g, 23.6 mmol), diethyl 2-hydroxyethoxymethanephosphonate, 2b, (5.0 g, 23.6 mmol) and triphenylphosphine (9.2 g, 35.4 mmol) in anhydrous DMF (70 mL) was stirred at ambient temperature under N$_2$ for 30 min. The reaction mixture was then cooled to 0° C. and diethyl azodicarboxylate (DEAD, 6.2 g, 35.4 mmol) in anhydrous DMF (25 mL) was added dropwise. The reaction mixture was allowed to warm to ambient temperature gradually and stirred overnight. Any unreacted adenine was filtered and the filtrate concentrated to dryness under vacuum. The crude product was purified by silica gel column chromatography, eluting with CH$_2$Cl$_2$/MeOH (9:1), to afford 3.3 g (43% yield) of the desired N$^9$-product 1a. mp. 136°–137° C. after recrystallization from EtOAc (Lit.[11] 137° C.). $^1$H NMR (CDCl$_3$) δ 8.35 (s, 1 H, H-2), 7.96 (s, 1 H, H-8), 6.28 (s, 2 H, NH$_2$), 4.42 (t, J=4.9 Hz, 2 H, CH$_2$N), 4.10 (apparent quintet, J=7.1 Hz, 4 H, 2 CH$_2$O), 3.94 (t, J=4.9 Hz, 2 H, CH$_2$O), 3.78 (d, J=8.4 Hz, 2 H, CH$_2$P), 1.30 (t,J=7.1 Hz, 6 H, 2 CH$_3$). $^{13}$C NMR (CDCl$_3$) δ 155.67, 152.89, 149.83, 141.37, 119.32 (adenine ring carbons), 71.24 (d, $^{2J}$C,P=10.6 Hz, OCH$_2$CH$_3$), 65.27 (d, $^{1J}$C,P=166.7 Hz, CH$_2$P), 62.46 (d, $^{3J}$C,P=6.6 Hz, CH$_2$O), 43.40 (CH$_2$N), 16.42 (d, $^{3J}$C,P=5.7 Hz, CH$_3$); UV (MeOH) λ$_{max}$ 260 (12, 900) nm. IR (KBr, cm$^{-1}$) 3275 and 3111 (vs, broad, NH$_2$), 1671 and 1603 (vs, adenine ring), 1240 (vs, P=O), 1045 and 1024 (vs, P—O—C and C—O—C); MS (CI) m/e 330 (100, M+1); Anal. calcd. for C$_{12}$H$_{20}$N$_5$O$_4$P: C, 43.75; H, 6.12; N, 21.27. Found: C, 43.80; H, 6.03; N, 21.23.

Example 5

6-Chloro-9-(2-diethoxyphosphonylmethoxyethyl) purine (1b)

The procedure employed for synthesis of 1a was followed for synthesis of 1b. Thus, 6-chloropurine (0.73 g, 4.72 mmol) was treated with diethyl 2-hydroxyethoxymethanephosphonate 2b (1.0 g, 4.72 mmol) in the presence of triphenylphosphine (1.6 g, 6.25 mmol) and diethyl azodicarboxylate (1.1 g, 6.25 mmol) in anhydrous DMF (14 mL). After purification by silica gel column chromatography eluting with CH$_2$Cl$_2$/MeOH (19:1), 0.82 g (50% yield) of the desired product 1b was obtained as a thick oil. $^1$H NMR (CDCl$_3$) δ 8.73 (s, 1 H, H-2), 8.27 (s, 1 H, H-8), 4.52 (t, J=4.9 Hz, 2 H, CH$_2$N), 4.10 (apparent quintet, J=7.5 Hz, 4 H, 2 OCH$_2$CH$_3$), 3.95 (t, J=4.9 Hz, 2 H, CH$_2$O), 3.78 (d, J=11.1 Hz, 2 H, CH$_2$P), 1.29 (t, J=7.0 Hz, 6 H, 2 CH$_3$); $^{13}$C NMR (CDCl$_3$) δ 151.79, 151.65, 150.87, 146.19, 131.38 (purine ring carbons), 70.66 (d, $^{2J}$C,P=10.1 Hz, OCH$_2$CH$_3$), 65.21 (d, $^{1J}$C,P=166.9 Hz, CH$_2$P), 62.44 (d, $^{3J}$C,P=6.5 Hz, CH$_2$O), 43.88 (CH$_2$N), 16.41 (d, $^{3J}$C,P=4.1, CH$_3$); IR (KBr, cm$^{-1}$) 1593 and 1562 (s, purine ring), 1225 (vs, P=O), 1026 (vs, shoulder, P—O—C and C—O—C); MS (CI) m/e 351 and 349 (67.8, 100, M+1), 315 (73.6, M—Cl+2), 313 (25.5, M—Cl); UV (MeOH) λ$_{max}$ 264 (9,593) nm; Anal. Calcd. for C$_{12}$H$_{18}$ClN$_4$O$_4$P: C, 41.31; H, 5.20; N 16.07. Found: C, 41.02; H, 5.32; N, 15.43.

Example 7

2,6-Diamino-9-(2-diethoxyphosphonomethoxyethyl) purine (1c)

A mixture of 2,6-diaminopurine (350 mg, 2.36 mmol), diethyl 2-hydroxyethoxymethane-phosphonate 2b (500 mg, 2.36 mmol) and triphenylphosphine (930 mg, 3.54 mmol) in anhydrous DMF (10 mL) was stirred at ambient temperature under N$_2$ for 30 min. The reaction mixture was then cooled to −30° C. and diethyl azodicarboxylate (0.56 mL, 3.54 mmol) was added dropwise at such a rate that the reaction temperature was maintained below −25° C. The reaction mixture was stirred at that temperature for 2 h and then allowed to warm to ambient temperature gradually and stirred overnight. Any unreacted 2,6-diaminopurine was removed by filtration and the solvent removed under vacuum. The crude product was purified by silica gel column chromatography, eluting with CH$_2$Cl$_2$/MeOH (9:1), to afford 190 mg (23 % yield) of the desired N$^9$- product 1c. An analytical sample was obtained from recrystallization using EtOAc/MeOH (5:1). mp. 152°–154° C. $^1$H NMR (CDCl$_3$) δ 7.66 (s, 1 H, H-8), 6.67 (s, 2 H, NH$_2$), 5.79 (s, 2 H, NH$_2$), 4.13 (t, J=5.0 Hz, 2 H, CH$_2$N), 3.95 (apparent quintet, J=7.3 Hz, 4 H, 2 OCH$_2$CH$_3$), 3.84 (d, J=8.4 Hz, 2 H, CH$_2$P), 3.81 (t, J=5.0 Hz, 2 H, CH$_2$O), 1.17 (t, J=7.1 Hz, 6 H, 2 CH$_3$); $^{13}$C NMR (CDCl$_3$) d 160.01, 156.08, 151.87, 138.79, 114.03 (purine ring carbons), 71.36 (d, $^{2JC,P}$=10.8 Hz, OCH$_2$CH$_3$), 65.26 (d, $^{1J}$C,P=166.5 Hz, CH$_2$P), 62.50 (d, $^{3J}$C,P=6.5 Hz, CH$_2$O), 42.92 (CH$_2$N), 16.44 (d, $^{3J}$C,P=5.7 Hz, CH$_3$); UV (MeOH) $\lambda_{max}$ 255 (10,300), 281(12,000) nm; IR (KBr, cm$^{-1}$) 3345 and 3177 (s, broad, NH$_2$), 1669, 1636 and 1599 (s, purine ring), 1242 (s, P=O), 1020 (s, P—O—C); MS (CI) m/e 345 (100, M+1), 344 (29.5, M$^+$); Anal. calcd. for C$_{12}$H$_{21}$N$_6$O$_4$P.1/4H$_2$O: C, 41.32; H. 6.21; N, 24.09. Found: C, 41.36; H. 6.02; N, 23.72.

Example 8

2-Amino-6-chloro-9-(2-diethoxyphosphonomethoxyethyl)purine (1d)

A mixture of 2-amino-6-chloropurine (890 mg, 4.2 mmol), diethyl 2-hydroxyethoxymethane-phosphonate 2b (710 mg, 4.2 mmol) and triphenylphosphine (1.65 g, 6.3 mmol) in anhydrous DMF (10 mL) was stirred at ambient temperature under N$_2$ for 30 min. The reaction mixture was then cooled to −10° C. and diethyl azodicarboxylate (0.67 mL, 4.2 mmol) in DMF (2 mL) was added dropwise at such a rate that the reaction temperature was maintained at −10° C. The reaction mixture was stirred at that temperature for 2 h and then allowed to warm to ambient temperature gradually and stirred for 5 h. Any unreacted 2-amino-6-chloropurine was removed by filtration and the solvent removed under vacuum. The crude product was purified by silica gel column chromatography, eluting with CH$_2$Cl$_2$/MeOH (9:1), to afford 650 mg (42 % yield) of the desired N$^9$-product 1d. $^1$H NMR (CDCl$_3$) δ 7.90 (s, 1 H, H-8), 5.20 (s, broad, 2 H, NH$_2$), 4.30 (t, J=4.8 Hz, 2 H, CH$_2$N), 4.12 (dq, J=8.4 Hz, J=7.0 Hz, 4 H, 2 OCH$_2$CH$_3$), 3.92 (t, J=5.0 Hz, 2 H, CH$_2$O), 3.79 (d, J=8.4 Hz, 2 H, CH$_2$O), 1.30 (t, J=7.1 Hz, 6 H, 2 CH$_3$); $^{13}$C NMR (CDCl$_3$) δ 159.20, 153.78, 151.20, 143.29, 124.99 (purine ring carbons), 70.82 (d, $^{2J}$C,P=10.3 Hz, OCH$_2$CH$_3$), 65.17 (d, $^{1J}$C,P=166.0 Hz, CH$_2$P), 62.42 (d, $^{3J}$C,P=5.7 Hz, CH$_2$O), 43.19 (CH$_2$N), 16.27 (d, $^{3J}$,P=5.7 Hz, CH$_3$); UV (MeOH) $\lambda_{max}$ 247 (14,600), 310 (18,300) nm; IR (KBr, cm$^{-1}$) 3327 and 3210 (m, broad, NH$_2$), 1612 and 1562 (vs, purine ring), 1229 (s, P=O), 1026 (s, P—O—C); MS (CI) m/e 366 and 364 (40.5, 100, M+1), 3328 (22.3, M—Cl); Anal. calcd. for C$_{12}$H$_{19}$ClN$_5$O$_4$P: C, 39.63; H, 5.26; N, 19.25. Found: C, 39.53; H, 5.48; N, 18.99.

Example 9

9-[2-(Phosphonomethoxy)ethyl]adenine (PMEA)

9-[2-(Diethylphosphonomethoxy)ethyl]adenine, 1a (100 mg, 0.30 mmol), was dissolved in anhydrous dichloromethane (2 mL). Bromotrimethylsilane (0.4 mL, 3.0 mmol) was added dropwise to the stirred solution at ambient temperature. After the addition was completed, the reaction mixture was stirred for 2.5 h, whereupon the mixture was evaporated under vacuum to afford a white foam solid, mp. 145°–150° C., which was then dissolved in H$_2$O (1 mL). Acetone (2 mL) was added to the aqueous solution and a white solid precipitate was formed and collected by filtration to afford 40 mg (49% yield) of the desired product PMEA. mp. 278° C. (dec.) (Lit. $^{11}$ did not melt up to 250° C.). $^1$H NMR (DMSO-d$_6$) δ 8.15 and 8.14 (2 s, 2 H, H-2, H-8), 7.35 (s, 2 H, NH$_2$, disappeared with D$_2$O exchange), 4.32 (t, J=5.1 Hz, 2 H, CH$_2$N), 3.87 (t, J=5.2 Hz, 2 H, CH$_2$O), 3.60 (d, J=8.7 Hz, 2 H, CH$_2$P); IR (KBr, cm$^{-1}$) 3403–2733 (s, broad, OH and NH$_2$), 1694 (vs) and 1599 (m) (purine ring), 1225 (vs, P=O); MS (FAB) m/e 274 (100, M+1); UV (H$_2$O) $\lambda_{max}$ 260 (13,900) nm; Anal. calcd. for C$_8$H$_{12}$N$_5$O$_4$P.1/4H$_2$O: C, 34.60; H, 4.54; N, 25.22. Found: C, 34.58; H, 4.66; N, 24.66.

References

1. Hughes, D. L. *Org. React.* 1992, 42, 335–656.
2. Jenny, T. F.; Previsani, N.; Benner, S. A. *Tetrahedron Lett.* 1991, 32, 7029–7032.
3. Bonnal, C.; Chavis, C.; Lucas, M. *J. Chem. Soc. Perkin Trans.* 1 1994, 1401–1410.
4. Overberger, C. G.; Chang, J. Y. *Tetrahedron Lett.* 1989, 30, 51–54.
5. De Clercq, E.; Holy, A.; Rosenberg, I.; Sakuma, T.; Balzarini, J.; Maudgal, P. C. *Nature* 1986, 323, 464–467.
6. De Clercq, E.; Sakuma, T.; Baba, M.; Pauwels, R.; Balzarini, J.; Rosenberg, I.; Holy, A. *Antiviral Res.* 1987, 8, 261–272.
7. Heijtink, R. A.; Kruining, J.; De Wilde, G. A.; Balzarini, J.; De Clercq, E.; Schalm. S. W. *Antimicrob. Agents Chemother.* 1994, 38, 2180–2182.
8. Pauwels, R.; Balzarini, J.; Schols, D.; Baba, M.; Desmyter, J.; Rosenberg, I.; Holy, A.; De Clercq, E. *Antimicrob. Agents Chemother.* 1988, 32, 1025–1030.
9. Balzarini, J.; Naesens, L.; Herdewijn, P.; Rosenberg, I.; Holy, A.; Pauwels, R.; Baba, M.; Jones, D. G.; De Clercq, E. *Proc. Nati. Acad. Sci. USA* 1989, 86, 332–336.
10. Gong, Y.-F.; Marshall, D. R.; Srinivas, R. V.; Fridland, A. *Antimicrob. Agents Chemother.* 1994, 38, 1683–1687.
11. Holy, A.; Rosenberg, I. *Collect. Czech. Chem. Commun.* 1987, 52, 2801–2809.
12. Holy, A.; De Clercq, E.; Votruba, I. In *Nucleotide Analogues as Antiviral Agents*; Martin, J. C. Ed.; ACS Washington, D. C., 1989; Chapter 4, pp 51–71.
13. Bronson, J. J.; Kim, C. U.; Ghazzouli, I.; Hitchcock, M. J. M.; Kern, E. R.; Martin, J. C. see ref. 12, Chapter 5, pp 72–87.
14. Bailey, W. F.; Zarcone, L. M.; Rivera, A. D. *J. Org. Chem.* 1995, 60, 2532–2536.
15. Webb, R. R., Jr., et al. *European Patent Publication* 0269947B1, 1992.
16. Arbuzov, B. A.; Ukhvatova, E. N. *Zh. Obshch. Khim.* 1959, 29, 503–507.
17. Tsuoda, T.; Yamamiya, Y.; Kawamura, Y.; Ito, S. *Tetrahedron Lett.* 1995, 36, 2529–2530.

What we claim:
1. A method for the preparation of a compound of formula I:

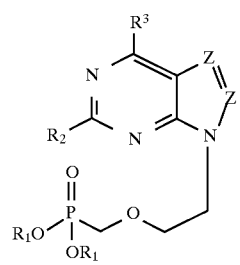

wherein Z represents N or CH; R$_1$ represents hydrogen, alkyl, aryl, or arylalkyl; R$_2$ and R$_3$ are independently selected from H, OH, halo, NH$_2$, C$_6$H$_5$CH$_2$O, or R$_4$R$_5$N wherein R4 and R$_5$ are independently selected from alkyl, aryl, or arylalkyl, said method comprising reacting a compound of formula II with a compound of formula III;

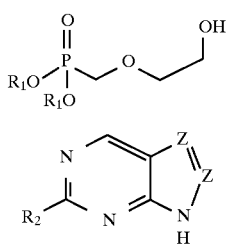

wherein Z, $R_1$, $R_2$ and $R_3$ are defined above, in the presence of an azo compound and a phosphorus derivative.

2. The method of claim 1, further comprising the step of hydrolyzing a first compound of formula I wherein $R_1$ represents alkyl, aryl, or arylkyl to produce a second compound of formula I wherein $R_1$ represents hydrogen.

3. The method of claim 2, wherein said hydrolyzing is performed with a trimethylsilyl halide.

4. The method of claim 1, wherein the azo compound is a member selected from the group consisting of diethyl azodicarboxylate, diisopropyl azodicarboxylate, dibutyl azodicarboxylate, dipiperidinoazodicarboxamide, bis($N^4$-methylpiperazin-1-yl)azodicarboxamide, dimorpholinoazodicarboxamide, and N,N,N',N'-tetramethylazodicarboxamide.

5. The method of claim 1, wherein the phosphorous derivative is a member selected from the group consisting of triphenylphosphine, tri-n-butylphosphine, triethylphosphine, trimethylphosphine and tris(dimethylamino)phosphine.

6. The method of claim 1, wherein the azo compound is diethyl azo dicarboxylate and the phosphorus derivative is triphenylphosphine.

* * * * *

UNITED STATES PATENT AND TRADEMARK OFFICE
CERTIFICATE OF CORRECTION

PATENT NO. : 5,874,577
DATED : February 23, 1999
INVENTOR(S) : Chen et al

It is certified that error appears in the above-identified patent and that said Letters Patent is hereby corrected as shown below:

On the title page: Item [75]

Delete "Method for the Preparing [9-12-(Diethoxyphosphonomethoxy)ethyl]adenine and analogues thereof" and insert --Method for Preparing 9-[2-(Diethoxyphosphonomethoxy)ethyl]Adenine and analogues thereof--.

Signed and Sealed this

Twenty-seventh Day of April, 1999

Attest:

Attesting Officer

Q. TODD DICKINSON

Acting Commissioner of Patents and Trademarks